United States Patent [19]
Gupta

[11] Patent Number: 5,476,971
[45] Date of Patent: Dec. 19, 1995

[54] GLYCERINE DITERTIARY BUTYL ETHER PREPARATION

[75] Inventor: Vijai P. Gupta, Berwyn, Pa.

[73] Assignee: ARCO Chemical Technology, L.P., Greenville, Del.

[21] Appl. No.: 373,672

[22] Filed: Jan. 13, 1995

[51] Int. Cl.$^6$ .......................... C07C 43/11; C07C 43/13
[52] U.S. Cl. .......................... 568/619; 568/613; 568/617; 568/618
[58] Field of Search .................................. 568/613, 617, 568/618, 619

[56] References Cited

U.S. PATENT DOCUMENTS

| | | | |
|---|---|---|---|
| 1,968,033 | 7/1934 | Evans et al. | 568/619 |
| 4,270,008 | 5/1981 | Weber et al. | 568/448 |
| 4,980,511 | 12/1990 | Hoelderich et al. | 568/310 |
| 5,308,365 | 5/1994 | Kesling et al. | 44/447 |
| 5,312,995 | 5/1994 | Faraj | 568/427 |

FOREIGN PATENT DOCUMENTS

| | | |
|---|---|---|
| 0282902 | 9/1988 | European Pat. Off. . |
| 0480482 | 4/1992 | European Pat. Off. . |
| 4222183 | 1/1994 | Germany . |
| 2205835 | 12/1988 | United Kingdom . |

*Primary Examiner*—Werren B. Lone
*Attorney, Agent, or Firm*—William C. Long

[57] ABSTRACT

Glycerine di-t-butyl ether is prepared by the liquid phase reaction of glycerine and the reaction being carried out with separate liquid phases comprised of isobutylene and glycerine.

5 Claims, 1 Drawing Sheet

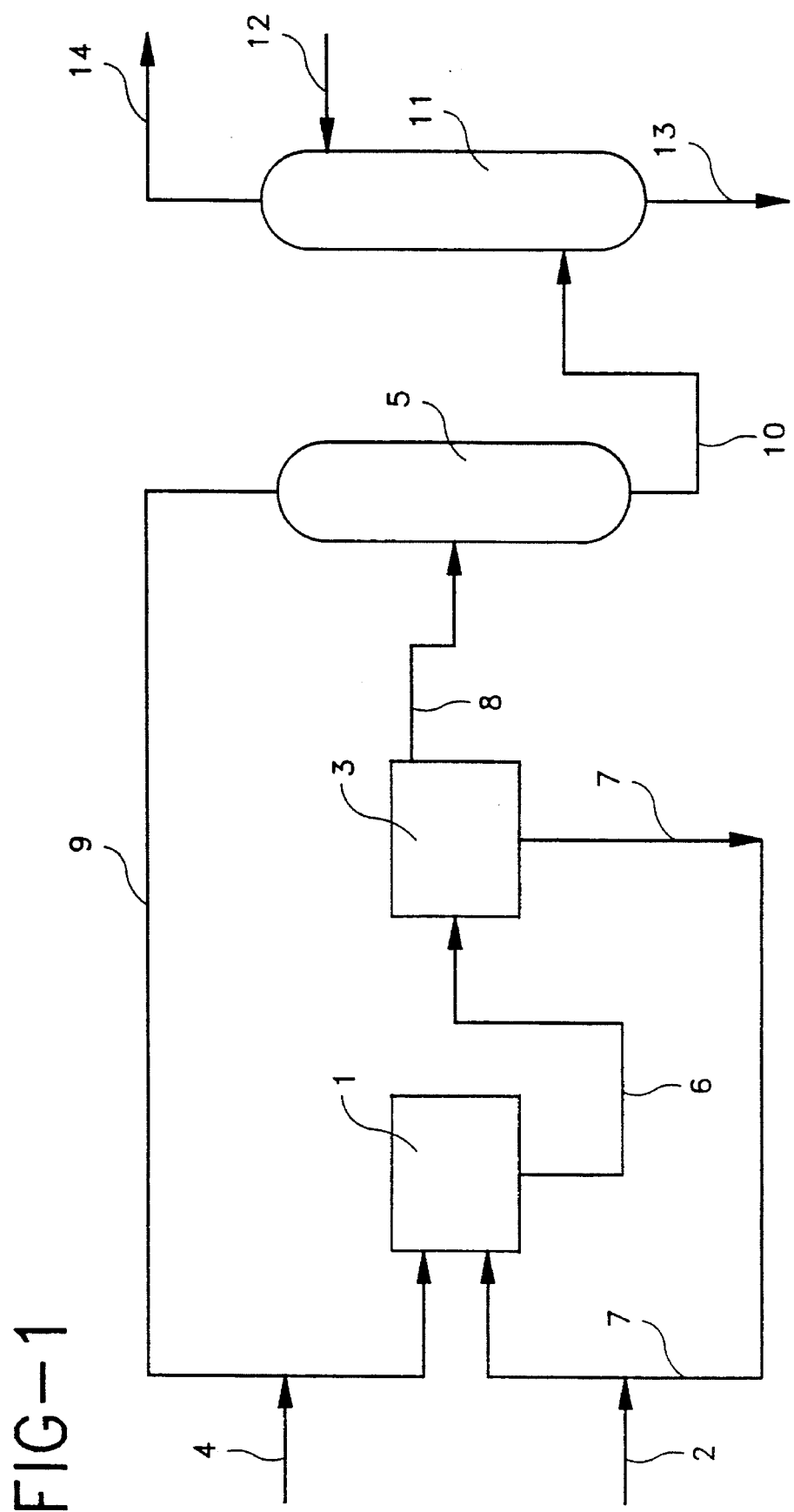

GLYCERINE DITERTIARY BUTYL ETHER PREPARATION

BACKGROUND OF THE INVENTION

1. Field of the Invention

The present invention relates to the preparation of glycerine ditertiary butyl ether by reaction of isobutylene with glycerine in a two phase mode and includes the phase separation of the reaction effluent and recycle of the polar phase which contains unreacted glycerine as well as glycerine monotertiary butyl ether.

2. Description of the Prior Art

The preparation of polyol alkyl ethers by reaction of an olefin such as isobutylene with a polyol such as glycerine using an acid catalyst is a known reaction.

U.S. Pat. No. 1,968,033 teaches this reaction using, for example, a sulfuric acid catalyst.

Published German Application No. P 4,222,183.8 teaches this reaction using soluble or insoluble acid catalysts such as p-toluenesulfonic acid, sulfoacetic acid, sulfosuccinic acid, sulfotriacetin, and dodecylbenzenesulfonic acid.

U.S. Pat. No. 5,308,365 teaches this reaction using a highly cross-linked sulfonic acid ion exchange resin such as Amberlyst XN1010 catalyst.

In the processes of the prior art, difficulties have been encountered in the recovery of reaction products from the etherification reaction mixtures, and in the production of particular desired ether products from among the several possible products.

BRIEF DESCRIPTION OF THE INVENTION

In accordance with the present invention, the reaction of glycerine with isobutylene is carried out in the liquid phase in a two phase reaction system, one phase being a glycerine-rich polar phase and the other phase being an olefin-rich hydrocarbon phase. An acidic catalyst is employed which is primarily contained in the polar glycerine phase. The reaction mixture is phase separated into the heavier glycerine and catalyst containing polar phase which is conveniently recycled, and a lighter hydrocarbon phase from which product ethers can be readily separated.

DESCRIPTION OF THE DRAWING

The accompanying drawing illustrates schematically practice of the invention.

DETAILED DESCRIPTION

Referring to the accompanying drawing, there is described therein an embodiment of the invention where glycerine is continuously reacted with isobutylene to form alkyl diether product. The acid catalyzed reaction of glycerine and isobutylene takes place in reaction zone 1 which is, for example, a CSTR, and in which the reactants are maintained in two distinct liquid phases.

Net feed glycerine and make up catalyst as needed are fed via line 2, together with a recycle glycerine phase from decantation zone 3, to reaction zone 1 while net feed isobutylene is fed via line 4, together with recycle isobutylene from stripper 5, to reaction zone 1. It is necessary that the net glycerine and isobutylene fed to zone 1 comprise more than 1 mol up to 2 mols isobutylene per mol of glycerine. More isobutylene can be employed and this will result in tri-ether production.

The acid catalyst which is employed, e.g. p-toluenesulfonic acid, methane sulfonic acid, and the like, is contained primarily in the glycerine phase in reaction zone 1. The isobutylene and glycerine are substantially immiscible and with suitable agitation form two phases in reaction zone 1, a polar glycerine phase and an isobutylene phase. There is some isobutylene dissolved in the glycerine phase and most of the etherification reaction occurs in this phase. Mass transfer from the isobutylene phase to the glycerine phase maintains the supply of isobutylene in the glycerine phase.

Mono t-butyl glycerine formed in the glycerine phase will mainly remain in this phase. However, di-t-butyl glycerine product will preferentially transfer to the isobutylene phase. Because the great bulk of the catalytic etherification takes place in the glycerine phase, there is a substantially reduced tendency for di-t-butyl glycerine to further react to form the less desirable tri-t-butyl glycerine.

The reaction mixture is removed from reaction zone 1 and passes via line 6 to decantation zone 3 where it separates into an upper isobutylene phase comprised of mono-t-butyl glycerine, di-t-butyl glycerine and tri-t-butyl glycerine in addition to the unreacted isobutylene, and a lower glycerine phase comprised of glycerine, mono-t-butyl glycerine, catalyst and small amounts of di- and tri-t-butyl glycerine.

The glycerine phase passes via line 7 back to reaction zone 1 together with net feed glycerine and make up catalyst. The isobutylene phase passes from decantation zone 3 via line 8 to stripping column 5 wherein unreacted isobutylene is stripped overhead and passes via line 9 back to reaction zone 1 along with net feed isobutylene.

The bottom stream from stripper 5 comprises a small amount of catalyst, glycerine and mono-t-butyl glycerine as well as the di-t-butyl glycerine and tri-t-butyl glycerine products. This bottoms stream passes via line 10 to water wash column 11 wherein it is contacted with water which is introduced via line 12. Glycerine, catalyst and mono-t-butyl glycerine are extracted in the water and are removed via line 13 for recovery or disposal. This stream can be recycled to reaction zone 1 after water removal (not shown).

Product di-t-butyl glycerine together with such tri-t-butyl glycerine as is formed in reaction zone 1 is recovered via line 14.

A special advantage of the invention is that distillation of the high boiling glycerine and glycerine ethers can be avoided. Another advantage is that the less desirable mono-t-butyl ether product is conveniently separated and recycled to the reaction zone for conversion to the more valuable di-t-butyl ether while the further reaction of di-t-butyl glycerine to the tri-t-butyl ether is substantially suppressed. The di-t-butyl glycerine produced in accordance with the invention is a mixture of predominantly 1,3-di-t-butyl glycerine together with lesser amounts of 1,2 di-t-butyl glycerine.

Several embodiments of the invention can readily be practiced. In an embodiment, an inert non-polar solvent such as pentane, hexane or the like can be employed. The use of such a solvent is thought to aid in the phase separation and would lower operating pressure. Also, use of the non-polar solvent permit the use of lower concentrations of isobutylene. The use of a non-polar solvent is, however, not necessary.

As above indicated, it is necessary that the net feed to the etherification comprise at least one mol up to two mols of olefin per mol of glycerine.

It is also important that the reaction mixture in the etherification zone be maintained such that the polar glycerine phase comprises at least 30 wt % of the total reaction mixture, and that the glycerine content of the polar glycerine phase comprise at least 50 wt % and preferably at least 60 wt % of the polar phase.

Reaction conditions which are employed for the etherification are temperatures of about 40°–150° C., preferably about 50°–100° C. Pressures are sufficient to maintain the liquid phase, e.g. about 30 to 300 psig. Catalyst is employed in amounts of about 0.1 to 5.0 wt % of the reaction mixture, preferably about 0.5 to 2.5%.

The following example illustrates practice of the invention.

Referring to the accompanying drawing, isobutylene is continuously reacted with glycerine to form di-t-butyl glycerine product which is primarily 1,3 di-tertiary butyl glycerine.

About 51 lbs/hr of net glycerine feed is fed via line 2 to reaction zone 1 together with the recycle polar phase from decantation zone 3. About 46 lbs/hr of isobutylene is fed to zone 1 via line 4 together with a recycle hydrocarbon mixture from stripper 5.

Reactor 1 is a well agitated continuously stirred tank reactor, reaction conditions are maintained at 60° C. and 100 psig. In reactor 1 there is maintained a polar glycerine phase comprising 37% by weight of the total reaction mixture and an organic isobutylene phase comprising 63% of the reaction mixture.

Residence time in reactor 1 is about 2.5 hours.

About 258 lbs/hr of liquid reaction mixture passes from reactor 1 via line 6 to decantation zone where the reaction mixture phase separates into a lower polar glycerine phase and an upper organic hydrocarbon phase. The lower glycerine phase has a composition by weight of 65% glycerine, 30% mono-tertiary butyl glycerine, and 2% para-toluene sulfonic acid, and this phase is recycled via line 7 to reactor 1 at the rate of 96 lbs/hr.

The upper organic phase passes at the rate of 162 lbs/hr to stripper 5 wherein 65 lbs/hr isobutylene is stripped overhead at 38° C. and 60 psia and recycled via line 9 to reactor 1.

A bottom stream comprised by weight of 53% di-tertiary butyl glycerine, 44% mono-tertiary butyl glycerine, 1.5% tri-tertiary butyl glycerine, 1.5% glycerine and a trace of para-toluene sulfonic acid passes at the rate of 97 lbs/hr to extraction zone 11. Water is introduced into zone 11 via line 12 at the rate of 49 lbs/hr and countercurrently extracts glycerine, catalyst and monotertiary butyl glycerine and is removed via line 13 at the rate of 93 lbs/hr for disposal or recovery of the various components.

The organic phase is recovered from zone 11 via line 14 at the rate of 52 lbs/hr. This product stream comprises a trace of monotertiary butyl glycerine and 97% di-tertiary butyl glycerine and 3% tri-tertiary butyl glycerine, by weight.

As can be seen from the above, practice of the invention provides the means for selective production of the valuable di-tertiary butyl glycerine while suppressing formation of the less desirable tri-tertiary butyl glycerine.

I claim:

1. In a process for the preparation of di-t-butyl glycerine by reaction of isobutylene with glycerine, the improvement which comprises carrying out the reaction in the liquid phase while maintaining separate phases comprised of a polar glycerine phase and an isobutylene phase.

2. The process of claim 1 wherein the glycerine phase comprises at least 30% by weight of the reaction mixture.

3. The process of claim 1 wherein the glycerin phase is comprised of at least 50 wt % glycerine.

4. The process of claim 1 wherein the glycerine phase is comprised of at least 60 wt % glycerine.

5. In a process for the preparation of di-t-butyl glycerine by reaction of isobutylene with glycerine, the improvement which comprises carrying out the reaction in the liquid phase while maintaining separate phases comprised of a polar glycerine phase and an isobutylene phase and recovering product di-t-butyl glycerine from the isobutylene phase.

\* \* \* \* \*